United States Patent
Waxman et al.

(10) Patent No.: US 8,642,833 B2
(45) Date of Patent: *Feb. 4, 2014

(54) ABSORBENT ARTICLE CONTAINING STRUCTURED FIBERS

(75) Inventors: David M. Waxman, Moorestown, NJ (US); Shih-Kuang Lien, Taichung (TW)

(73) Assignee: Harbor Linen LLC, Gibbsboro, NJ (US)

( * ) Notice: Subject to any disclaimer, the term of this patent is extended or adjusted under 35 U.S.C. 154(b) by 120 days.

This patent is subject to a terminal disclaimer.

(21) Appl. No.: 13/170,934

(22) Filed: Jun. 28, 2011

(65) Prior Publication Data

US 2011/0257618 A1    Oct. 20, 2011

Related U.S. Application Data

(63) Continuation-in-part of application No. 12/849,268, filed on Aug. 3, 2010.

(60) Provisional application No. 61/231,114, filed on Aug. 4, 2009.

(51) Int. Cl.
*A61F 13/15* (2006.01)
*A61F 13/20* (2006.01)

(52) U.S. Cl.
USPC ........... 604/367; 442/334; 604/374; 604/375; 604/378; 604/383

(58) Field of Classification Search
USPC .......... 442/334; 604/356–357, 374–375, 378, 604/383, 367
See application file for complete search history.

(56) References Cited

U.S. PATENT DOCUMENTS

| | | | |
|---|---|---|---|
| 3,623,939 A | 11/1971 | Ono et al. | |
| 4,707,409 A | 11/1987 | Phillips | |
| 5,057,368 A | 10/1991 | Largman et al. | |
| 5,200,248 A | 4/1993 | Thompson et al. | |
| 5,277,976 A | 1/1994 | Hogle et al. | |
| 5,290,269 A * | 3/1994 | Heiman | 604/378 |
| 5,314,743 A | 5/1994 | Meirowitz et al. | |
| 5,330,817 A * | 7/1994 | Arnott et al. | 428/85 |
| 5,342,336 A | 8/1994 | Meirowitz et al. | |
| 5,356,402 A * | 10/1994 | Gillies et al. | 604/375 |
| 5,458,963 A | 10/1995 | Meirowitz et al. | |
| 5,486,167 A * | 1/1996 | Dragoo et al. | 604/384 |
| 5,634,914 A | 6/1997 | Wilkes et al. | |
| 5,705,249 A * | 1/1998 | Takai et al. | 428/94 |

(Continued)

OTHER PUBLICATIONS

Office Action issued Mar. 15, 2012 in U.S. Appl. No. 12/849,268.

(Continued)

*Primary Examiner* — Jackie Ho
*Assistant Examiner* — Aundria Hairell
(74) *Attorney, Agent, or Firm* — Panitch Schwarze Belisario & Nadel LLP

(57) ABSTRACT

A reusable absorbent article includes a hydrophilic top layer, a soaking layer adjacent to and beneath the top layer, a substantially liquid impermeable layer adjacent to and beneath the soaking layer, and a backing layer adjacent to and beneath the substantially liquid impermeable layer. All of the layers are secured together to form a unitary structure. The soaking layer is a non-woven fabric having a plurality of hydrophobic fibers of a generally circular cross-sectional shape and a plurality of hydrophilic fibers of a non-circular cross-sectional shape.

13 Claims, 2 Drawing Sheets

(56) References Cited

U.S. PATENT DOCUMENTS

| | | |
|---|---|---|
| 5,972,505 A | 10/1999 | Phillips et al. |
| 6,309,377 B1 | 10/2001 | Tsujiyama et al. |
| 6,344,595 B1 | 2/2002 | Phillips et al. |
| 6,352,774 B1 | 3/2002 | Phillips et al. |
| 6,436,518 B1 | 8/2002 | Phillips et al. |
| 6,458,726 B1 | 10/2002 | Harrington et al. |
| 6,492,023 B1 | 12/2002 | Phillips et al. |
| 6,548,731 B2 | 4/2003 | Mizutani et al. |
| 6,593,256 B1 * | 7/2003 | Wildeman .................. 442/402 |
| 6,617,025 B1 | 9/2003 | Phillips et al. |
| 6,753,082 B1 | 6/2004 | Lobovsky et al. |
| 6,761,957 B1 | 7/2004 | Phillips et al. |
| 2004/0102751 A1 | 5/2004 | Schueler |
| 2004/0121681 A1 * | 6/2004 | Lindsay et al. .............. 442/121 |
| 2005/0176326 A1 | 8/2005 | Bond et al. |
| 2005/0227563 A1 | 10/2005 | Bond |
| 2005/0256757 A1 * | 11/2005 | Sierra et al. .................. 705/10 |

OTHER PUBLICATIONS

Office Action issued Dec. 24, 2012 in U.S. Appl. No. 12/849,268.
Office Action issued Aug. 3, 2012 in U.S. Appl. No. 12/849,268.

* cited by examiner

ABSORBENT ARTICLE CONTAINING STRUCTURED FIBERS

CROSS-REFERENCE TO RELATED APPLICATIONS

This application is a Continuation-In-Part of U.S. patent application Ser. No. 12/849,268, filed on Aug. 3, 2010 and entitled "Underpad," which claims the benefit of U.S. Provisional Patent Application No. 61/231,114, filed on Aug. 4, 2009 and entitled "Underpad," the disclosures of which are incorporated by reference herein.

BACKGROUND OF THE INVENTION

Persons who are elderly, handicapped, seriously injured or ill often face difficulties in performing the most common of daily activities, particularly if they are immobile or confined to their beds. As such, several products have been developed for and are used by these persons in their homes, hospitals or short- or long-term care facilities. Incontinence underpads, for example, are often used by medical professionals in caring for patients who cannot easily move around or are completely confined to their beds. Underpads acts as moisture barriers to protect surfaces, such as bedding, on which the user is resting, from damage caused by moisture voluntarily or involuntarily released by the user. Additionally, such underpads serve to enhance the comfort of the user or patient by absorbing such moisture so that the user is kept relatively dry. Reusable underpads, in particular, are also environmentally friendly because they need not be disposed of after each use, but rather can be laundered and used again.

Conventional reusable underpads have a multi-layered structure, wherein the top layer comprises a fabric made of a polyester and cotton blend and is quilted to an adjacent absorbent layer. Such underpads generally also have a vinyl barrier forming the bottom layer of the structure. However, such conventional reusable underpads are generally inferior for a number of reasons. For example, their typical construction cannot withstand a great number of launderings, particularly institutional or industrial launderings, without deteriorating. Further, they are often made of materials which do not absorb and disperse moisture effectively, such that the surface of the underpad in contact with the user or patient can often remain wet for a significant amount of time, which leads to the user or patient being uncomfortable.

It would therefore be beneficial to provide a reusable underpad which is resilient and which effectively absorbs and disperses moisture effectively to maximize the comfort of the user.

BRIEF SUMMARY OF THE INVENTION

Briefly stated, an embodiment of the present invention is directed to a reusable absorbent article including a hydrophilic top layer, a soaking layer adjacent to and beneath the top layer, a substantially liquid impermeable layer adjacent to and beneath the soaking layer, and a backing layer adjacent to and beneath the substantially liquid impermeable layer. All of the layers are secured together to form a unitary structure. The soaking layer is a non-woven fabric having a plurality of hydrophobic fibers of a generally circular cross-sectional shape and a plurality of hydrophilic fibers of a non-circular cross-sectional shape.

Another embodiment of the present invention is directed to a reusable absorbent article including a hydrophilic top layer, an absorbent layer adjacent to and beneath the top layer, a substantially liquid impermeable layer adjacent to and beneath the absorbent layer, and a backing layer adjacent to and beneath the substantially liquid impermeable layer. All of the layers are secured together to form a unitary structure. The absorbent layer comprises (i) a first non-woven fabric comprising a plurality of hydrophilic fibers and (ii) a second a non-woven fabric comprising a plurality of hydrophobic fibers and a plurality of hydrophilic fibers.

BRIEF DESCRIPTION OF THE DRAWINGS

The following detailed description of the invention will be better understood when read in conjunction with the appended drawings. For the purpose of illustrating the invention, there is shown in the drawings an embodiment which is presently preferred. It should be understood, however, that the invention is not limited to the precise arrangements and instrumentalities shown.

In the Drawings.

DETAILED DESCRIPTION OF THE INVENTION

Figure 1:
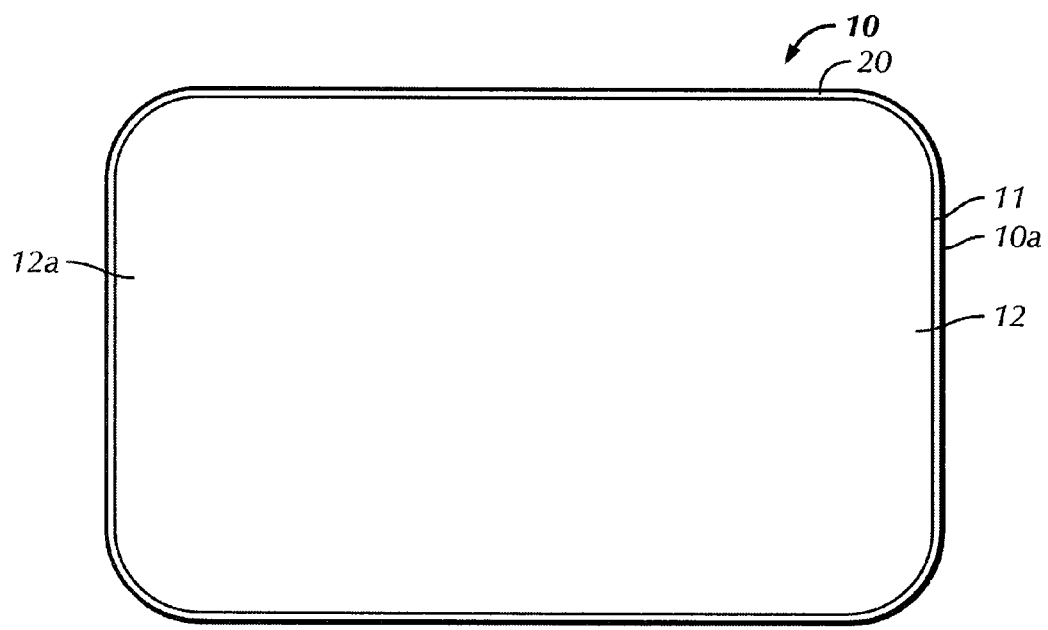
FIG. 1 is a top plan view of an underpad according to a preferred embodiment of the present invention.

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the underpad and designated parts thereof. Unless specifically set forth herein, the terms "a", "an" and "the" are not limited to one element but instead should be read as meaning "at least one". The terminology includes the words noted above, derivatives thereof and words of similar import.

Figure 2:
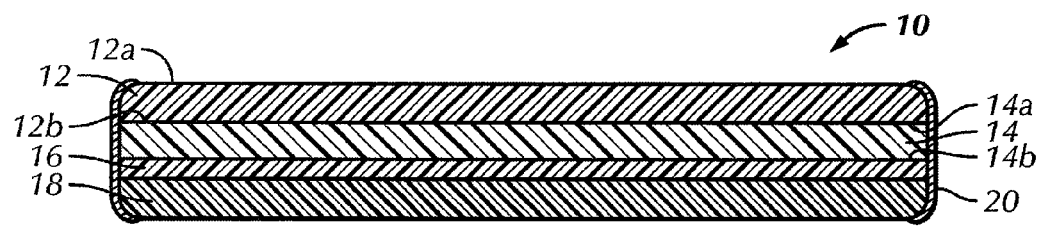
FIG. 2 is a cross-sectional side elevational view of the underpad shown in FIG. 1.

Referring to the drawings in detail, wherein like numerals and characters indicate like elements throughout, there are shown in FIGS. 1-2 a presently preferred embodiment of an underpad in accordance with the present invention. With reference initially to FIGS. 1-2, the underpad 10, includes a top layer 12 and a bottom layer 18.

With particular reference to FIGS. 1-2, the underpad 10 serves as a reusable and launderable incontinence pad and comprises a plurality of layers and, in particular, four layers. The first or top layer 12 is made of a hydrophilic material or of a material that has been subjected to a hydrophilic treatment. As such, the hydrophilic top layer 12 has a strong affinity for water and other fluids and, thus, readily absorbs moisture. A first or top surface 12a of the top layer 12 is in contact with the body of the user. The material of the top layer 12 is preferably a polyester brushed fabric, thereby providing a soft and comfortable surface in contact with the body of the user. However, it will be understood by those skilled in the art that any material having similar properties to a polyester brushed fabric may be used.

A second or intermediate absorbent layer 14 is disposed adjacent to and beneath or below the top layer 12. In particular, a top surface 14a of the second layer 14 is directly in contact with a second or bottom surface 12b of the top layer 12. The second layer 14 is an absorbent layer 14 that functions as a distribution or soaking layer 14, for absorption, containment and distribution of liquid. The soaking layer 14 has a thickness of approximately 2.5-3.0 millimeters, and a mass per unit area of 350 grams per square meter.

The soaking layer 14 is preferably made of a non-woven needle punch fabric and comprises a plurality of hydrophobic fibers and a plurality of hydrophilic fibers. The hydrophobic fibers are preferably polyester fibers and have a generally circular cross-sectional shape. The hydrophilic fibers, on the other hand, are shaped fibers, meaning they have a non-circular cross-sectional shape, and are preferably made of a polyester resin. The hydrophilic shaped fibers have a denier of approximately 3.0 and, more preferably, of 2.78, a length of approximately 3-5 centimeters and a diameter of approximately 4-5 microns. Preferably, the soaking layer 14 comprises approximately 60-65% polyester hydrophobic fibers and 35-40% hydrophilic fibers.

The hydrophilic shaped fibers facilitate the absorption of moisture away from the top layer 12 and dispersion of the absorbed moisture throughout the soaking layer 14 and, more particularly, toward a bottom surface 14b of the soaking layer 14. The hydrophobic polyester fibers facilitate containment of the absorbed moisture within the soaking layer 14. More specifically, the absorbed moisture is contained within the hydrophilic shaped fibers and between the hydrophobic polyester fibers.

Figure 3:
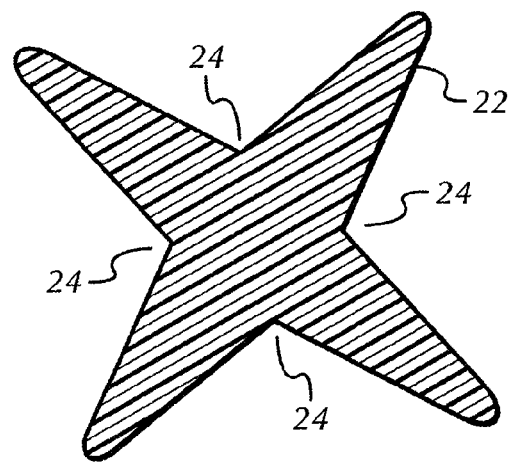
FIG. 3 is a cross-sectional view of a fiber of a layer of the underpad shown in FIG. 1.

The hydrophilic shaped fibers have a unique cross-section, as shown in FIG. 3, which enables them to absorb and disperse moisture quickly. Specifically, each hydrophilic shaped fiber 22 has a substantially "x"-shaped cross section. The notches 24 formed by the cross sectional shape of the fibers 22 create a siphoning effect to draw moisture away from the top layer 12 and to facilitate the movement of the absorbed moisture along the length of the fibers 22 and toward the bottom surface 14b of the soaking layer 14.

The hydrophilic shaped fibers 22 of the soaking layer 14 are quick-drying fibers and have a vertical wicking rate of approximately 5.7 millimeters per minute, significantly faster than that of cotton (3.3 millimeters per minute) and of nylon (1.7 millimeters per minute). Also, the hydrophilic shaped fibers 22 of the soaking layer 14 have a diffusion area of approximately 74.7 square millimeters per second, significantly larger than that of cotton (50 square millimeters per second) and of nylon (11.7 square millimeters per second).

Thus, because the soaking layer 14 comprises a combination of the shaped hydrophilic fibers 22 and circular hydrophobic fibers, the soaking layer 14 is formed of a breathable material which draws moisture away from the top layer 12 and the user's body and quickly absorbs and disperses the moisture. In particular, the absorbed moisture is quickly dispersed toward the bottom surface 14b of the soaking layer 14 and is contained within the soaking layer 14. Consequently, the top surface 12a of the top layer 12 quickly becomes dry after it is subjected to a release of moisture, thereby enhancing the comfort and dryness of the user.

Many conventional underpads utilize a polyester/rayon blend as the material of the soaking layer, where both fibers are of a circular cross-sectional shape. However, such fibers cannot absorb and disperse moisture as quickly as the shaped hydrophilic fibers. This is why the top surface of conventional underpads does not dry as quickly as the top surface 12a of the underpad 10.

A third layer 16 is disposed adjacent to and beneath or below the soaking layer 14, and is directly in contact with the bottom surface 14b of the soaking layer 14. The third layer 16 functions as a barrier layer which is substantially impermeable to liquid. The barrier layer 16 is preferably made of a high temperature resistant polymer film, such as a polyurethane film, which is a breathable and waterproof material. As such, the barrier layer 16 prevents absorbed moisture within the soaking layer 14 from passing therethrough. It will be understood by those skilled in the art that while a polyurethane film is described, the barrier layer 16 may comprise any polymer film having similar or equivalent properties to polyurethane. The barrier layer 16 has a thickness of approximately 25 to 30 micrometers and is attached to the fourth or bottom backing layer 18. Accordingly, the backing layer 18 is disposed adjacent to and beneath or below the barrier layer 16, and is in contact with the surface on which the user is resting, sitting, lying, etc. The bottom layer 18 is preferably made of a substantially liquid impermeable material that provides a non-slip surface between the underpad 10 and the surface on which the user is resting, sitting, lying, etc. Preferably, the bottom layer 18 is made of a polyester tricot fabric.

Because of the unique composition of the soaking layer 14, the underpad 10 has superior absorption properties and provides for maximum comfort of the user by keeping the user dry. In particular, the underpad 10 has a fluid holding capacity of approximately 2 liters per square meter and can hold a total of 1.6 liters of fluid. The underpad 10 also has an average surface wicking percentage of approximately 3% or less. In addition, the underpad 10 has an average speed of absorption of approximately 3 milliliters per second and an average speed of spread of the moisture of approximately 0.9 milliliters per second.

Further, all of the aforementioned materials used to form each layer 12, 14, 16, 18 of the underpad 10 have a superior ability to be processed (i.e., laundered) institutionally, thereby resulting in an underpad 10 that is durable and capable of withstanding several hundred launderings without suffering any significant changes or deterioration. The resilience of the underpad 10 is best demonstrated by a comparison of various properties and dimensions of the underpad 10 prior to and after laundering.

When it is initially manufactured, a preferred embodiment of the underpad 10 has a standard length of approximately 855 millimeters and an average length of approximately 860 millimeters. The underpad 10 has a standard width of approximately 912 millimeters and an average width of approximately 910 millimeters. The absorbent area of the underpad 10 is of a dimension of approximately 0.7 square meters and has a total mass of approximately 551 grams. The overall mass per unit area of the underpad 10 is 706 grams per square meters. The underpad 10 may be of any other suitable size, depending on the application for which it will be used.

Experiment 1

The underpad 10 was subjected to five launderings and various dimensions and properties of the laundered underpad 10 were measured. Notably, there was less than 5% shrinkage of the underpad 10. Specifically, after five launderings, the average length of the underpad 10 was 834 millimeters, a change of only about 2.4%, and the average width was 905 millimeters, a change of only about 0.8%. Further, the mass per unit area of the underpad 10 only changed slightly, to about 727 grams per square meter. Thus, the underpad 10 is clearly resilient and does not undergo significant changes in dimension when processed institutionally.

Further, after five launderings, the underpad 10 still had a fluid absorption capacity of 2 liters per square meter and an average surface wicking percentage of approximately 1.4%. The underpad 10 also had an average speed of absorption of approximately 3.2 milliliters per second and an average speed of spread of approximately 2.9 milliliters per second. Thus, the absorption capabilities of the underpad 10 remain superior and effective even after laundering.

Comparative Example 1

In order to further test the absorption properties of the underpad 10, 350 grams of water were applied to the underpad 10 and to a prior art known underpad. After three minutes, the top surfaces of both underpads were touched and observed. The top surface 12a of the underpad 10 was completely dry, while that of the prior art known underpad was still wet. Thus, the underpad 10 is clearly a quick-drying underpad and has superior absorption capabilities as compared with conventional underpads.

Figure 4:
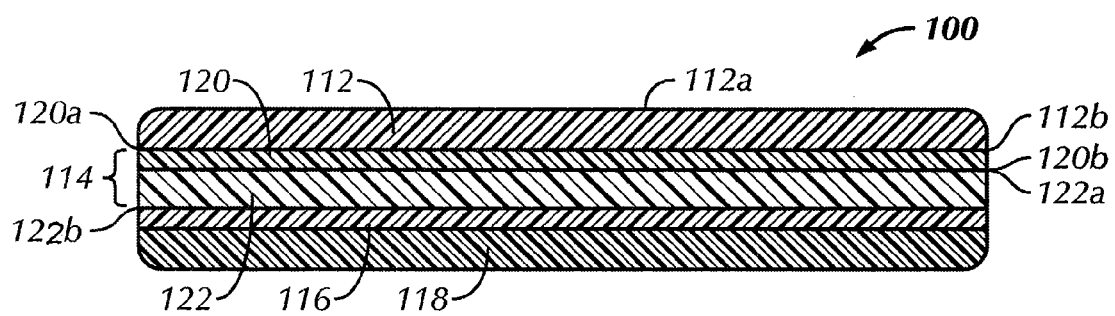
FIG. 4 is a cross-sectional side elevational view of an underpad in accordance with a second embodiment of the present invention.

FIG. 4 depicts an underpad 100 in accordance with a second preferred embodiment of the present invention. Similar to the underpad 10, the underpad 100 comprises a first or top layer 112, A second or intermediate absorbent layer 114 is disposed adjacent to and beneath or below the top layer 112, a third barrier layer 116 is disposed adjacent to and beneath or below the absorbent layer 114, and a fourth or bottom backing layer 118 attached to the barrier layer 116.

The top layer 112 has a first or top surface 112a and a second or bottom surface 112b, and is made of a hydrophilic material or of a material that has been subjected to a hydrophilic treatment. Thus, moisture is readily absorbed by and passes through the hydrophilically-treated top layer 112, and the top surface 112a of the top layer 112 in contact with the user is kept dry. The top layer 112 preferably comprises a synthetic polyester brushed fabric and, more preferably, is comprised substantially wholly of a hydrophilically-treated polyester brushed fabric for the comfort of the user. More preferably, the top layer 112 is comprised wholly of 50 denier polyester fibers. However, it will be understood by those skilled in the art that any material having similar properties to a polyester brushed fabric may be used. Preferably, the top layer 112 has a thread count of 24 and a thickness of approximately 0.30 to 0.35 millimeters. The top layer 112 also preferably has a mass per unit area of 85 to 95 grams per square meter, and more preferably 90 grams per square meter.

The absorbent layer 114 comprises a multi-layered and non-woven needle punch structure. Preferably, the absorbent layer 114 comprises a top layer or sheet 120 and a bottom layer or sheet 122 which is adjacent to and beneath the top sheet 120. The top sheet 120 and the bottom sheet 122 each has a top surface 120a, 122a and a bottom surface 120b, 122b, respectively. The top surface 120a of the top sheet 120 is directly in contact with the bottom surface 112b of the top layer 112. The bottom surface 120b of the top sheet 120 is directly in contact with the top surface 122a of the bottom sheet 122.

The top sheet 120 of the absorbent layer 114 preferably has a mass per unit area of 80 grams per square meter. The top sheet 120 is preferably made of a non-woven needle punch fabric and comprises a plurality of polyester fibers. More preferably, the top sheet 120 is comprised wholly of polyester fibers. Preferably, the polyester fibers of the top sheet 120 have a generally circular cross-sectional shape, a denier of approximately 14.0, and an average cut length of approximately 64 millimeters. The polyester fibers of the top sheet 120 are also preferably hydrophilic or hydrophilically treated, such that moisture is readily absorbed by the hydrophilically-treated polyester fibers of the top sheet 120.

The bottom sheet 122 is an absorbent sheet that functions as a distribution or soaking component for absorption, containment and distribution of liquid. More particularly, the bottom sheet 122 of the absorbent layer 114 preferably has a mass per unit area of 150 grams per square meter. The bottom sheet 122 is preferably made of a non-woven needle punch fabric and comprises a plurality of hydrophobic fibers and a plurality of hydrophilic fibers. More preferably, the bottom sheet 122 comprises approximately 70%-85% hydrophobic fibers and 15%-30% hydrophilic fibers.

The hydrophobic fibers of the bottom sheet 122 are preferably polyester fibers and have a generally circular cross-sectional shape. Preferably, the polyester fibers of the bottom sheet 122 are relatively fine fibers as compared with the polyester fibers of the top sheet 120. More particularly, the polyester fibers of the bottom sheet 122 preferably have a denier of approximately 2.0 to 2.5, and more preferably a denier of 2.2, significantly smaller than the preferred denier of the polyester fibers of the top sheet 120. The hydrophobic polyester fibers preferably have an average cut length of approximately 51 millimeters.

The hydrophilic fibers of the bottom sheet 122 are preferably viscose or rayon fibers. The hydrophilic viscose fibers of the bottom sheet 122 may have either a circular or non-circular cross-sectional shape. The hydrophilic viscose fibers preferably have a denier of 1.2 to 1.7, and more preferably are 1.5 denier fibers, and have an average cut length of approximately 51 millimeters. It will be understood by those skilled in the art that the lengths of the different fibers may be shortened or increased as necessary for the particular application in which the underpad 100 is to be used.

The non-woven top sheet 120 and the non-woven bottom sheet 122 are preferably needle punched together to form an integral structure. More particularly, the top sheet 120 and the bottom sheet 122 are needle punched together to form the non-woven needle punch fabric of the absorbent layer 114. The non-woven fabric of the absorbent layer 114 has a mass per unit area of 230 grams per square meter. Also, the absorbent layer 114 preferably has a thickness of 2.30 to 2.90 millimeters.

The absorbent layer 114 facilitates absorption, containment and distribution of liquid transported from the top layer 112. In particular, the top sheet 120 of the absorbent layer 114 serves as an additional layer of dryness protection for the user. Specifically, in addition to the top layer 112, moisture also readily passes through the hydrophilically-treated polyester fibers of the top sheet 120 to the bottom sheet 122 of the absorbent layer 114. In the bottom sheet 122, the hydrophilic viscose fibers facilitate the absorption of moisture away from the top sheet 120 and dispersion of the absorbed moisture throughout the bottom sheet 122 and, more particularly, toward the bottom surface 122b of the bottom sheet 122. The hydrophobic polyester fibers of the bottom sheet 122 facilitate containment of the absorbed moisture within the bottom sheet 122 of the absorbent layer 114. More specifically, in the bottom sheet 122, the absorbed moisture is contained within the hydrophilic viscose fibers and between the hydrophobic polyester fibers. Thus, the top layer 112 and the top sheet 120 of the absorbent layer 112 quickly become dry after being subjected to a release of moisture and are kept relatively dry during use, and the absorbed moisture is kept contained within the bottom sheet 122 of the absorbent layer 114 at a distance from the user. Consequently, the underpad 100 enhances the comfort and dryness of the user.

The barrier layer 116 is directly in contact with the bottom surface 122b of the bottom sheet 122 of the absorbent layer 114. As in the underpad 10, the barrier layer 116 of the underpad 100 is substantially impermeable to liquid and is preferably made of a high temperature resistant polymer film, such as a polyurethane film, which is a breathable and waterproof material. It will be understood by those skilled in the art that while a polyurethane film is described, the barrier layer 116 may comprise any polymer film having similar or equivalent properties to polyurethane. The barrier layer 116 has a thickness of approximately 25 to 30 micrometers.

The backing layer 118 is directly in contact with the surface on which the user is resting, sitting, lying, etc. The backing layer 118 of the underpad 100 is preferably made of a substantially liquid impermeable material that provides a non-slip surface between the underpad 100 and the surface on which the user is resting, sitting, lying, etc. Preferably, the bottom layer 118 is made of a brushed polyester tricot fabric which has been treated for water repellency. More preferably, the bottom layer 118 is comprised wholly of 50 denier polyester fibers. However, it will be understood by those skilled in the art that any material having similar properties to a polyester tricot fabric may be used. Preferably, the bottom layer 118 has a thread count of 24 and a thickness of approximately 0.30 to 0.35 millimeters. The backing layer 118 preferably has a mass per unit area of 80 to 90 grams per square meter, and more preferably 85 grams per square meter. The layers 112, 114, 116, 118 are assembled and secured or attached to each other and provided with a border 140, similar to the assembly of the underpad 10.

Because of the unique structure of the underpad 100, and particularly of the absorbent layer 114, the underpad 100 facilitates quick absorption and movement of moisture away from the surfaces in contact with or close to the user, and containment of the moisture within the center of the underpad 100. Thus, the underpad 100 provides for maximum comfort of the user by keeping the user dry.

As part of a performance analysis, the underpad 100 was subjected to five launderings and various properties of the laundered underpad 100 were measured. In particular, it was discovered that after five launderings, the underpad 100 has a fluid holding capacity of greater than approximately 300% relative to the overall weight of the underpad 100. The underpad 100 also has an average surface wicking percentage of less than approximately 2%. In addition, after five launderings, the underpad 100 has an average rate of absorption which is 20 to 40% faster than conventional industry standards, and an average rate of spread of the moisture which is 70 to 85% faster than conventional industry standards.

One or more of the layers 12, 14, 16, 18 or 112, 114, 116, 118 of the underpads 10, 100, respectively, may be secured or attached to each other by conventional means, such as by quilting, lamination, heat sealing, or with liquid adhesives. Preferably, the barrier layers 16, 116 are laminated to the respective bottom layers 18, 118. Preferably, referring to the construction of the underpad 10, once the layers 12, 14, 16, 18 are assembled and secured or attached to each other, a border 20 is provided to cover the edges of the layers 12, 14, 16, 18. The edges 10a of the underpad 10, covered by the border 20, are stitched together at a seam 11. The border 20 serves to keep the layers 12, 14, 16, 18 attached together, such that the layers 12, 14, 16, 18 form a unitary structure, and enhances the visual appearance of the underpad 10. The underpad 100 is formed in a similar manner and configuration.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A reusable absorbent article comprising:
   an outer surface having a substantially hydrophilic top layer;
   an absorbent layer adjacent to and beneath the top layer;
   a substantially liquid impermeable layer adjacent to and beneath the absorbent layer; and
   a backing layer adjacent to and beneath the substantially liquid impermeable layer, all of the layers being secured together to form a unitary structure,
      wherein the absorbent layer is secured to and distinct from the top layer and comprises (i) a first non-woven fabric comprising a plurality of hydrophilic polyester fibers and (ii) a second a non-woven fabric comprising approximately 70%-85% hydrophobic polyester fibers and approximately 15%-30% hydrophilic viscose fibers, and
      wherein the reusable absorbent article has a fluid holding capacity of greater than approximately 300% relative to a overall weight of the article.

2. The reusable absorbent article of claim 1, wherein the polyester fibers of the second non-woven fabric of the absorbent layer are finer than the polyester fibers of the first non-woven fabric of the absorbent layer.

3. The reusable absorbent article of claim 1, wherein the hydrophilic fibers of the first non-woven fabric of the absorbent layer have a generally circular cross-sectional shape.

4. The reusable absorbent article of claim 1, wherein the hydrophobic fibers of the second non-woven fabric of the absorbent layer have a generally circular cross-sectional shape.

5. The reusable absorbent article of claim 1, wherein the first non-woven fabric of the absorbent layer is comprised wholly of hydrophilic polyester fibers.

6. The reusable absorbent article of claim 1, wherein each of the first and second non-woven fabrics of the absorbent layer is a non-woven needle punch fabric.

7. The reusable absorbent article of claim 6, wherein the first and second non-woven fabrics of the absorbent layer are needle punched together to form an integral structure.

8. The reusable absorbent article of claim 1, wherein the top layer has a thickness of approximately 0.30 to 0.35 millimeters, the absorbent layer has a thickness of approximately 2.30 to 2.90 millimeters, the substantially liquid impermeable layer has a thickness of approximately 25 to 30 micrometers, and the backing layer has a thickness of approximately 0.30 to 0.35 millimeters.

9. The reusable absorbent article of claim 1, wherein the top layer has a mass per unit area of 85 to 95 grams per square meter.

10. The reusable absorbent article of claim 1, wherein the absorbent layer has a mass per unit area of 230 grams per square meter.

11. The reusable absorbent article of claim 1, wherein the backing layer has a mass per unit area of 80 to 90 grams per square meter.

12. The reusable absorbent article of claim 1, wherein the top layer, the soaking layer, the substantially liquid impermeable layer and the backing layer are independently fabricated and subsequently secured to each other at a stitched seam.

13. A reusable absorbent article comprising:
   an outer surface having a hydrophilic top layer, made of a polyester brushed fabric;
   a multilayered absorbent layer adjacent to and beneath the top layer, the absorbent layer being distinct from the top layer;

a substantially liquid impermeable polyurethane film adjacent to and beneath the absorbent layer; and a polyester tricot fabric backing layer adjacent to and beneath the substantially liquid impermeable layer, wherein all of the layers are secured together to form a unitary structure, and wherein the absorbent layer comprises (i) a first non-woven fabric comprising a plurality of hydrophilic polyester fibers of a generally circular cross-sectional shape and (ii) a second non-woven fabric comprising a plurality of hydrophobic polyester fibers of a generally circular cross-sectional shape and a plurality of hydrophilic viscose fibers.

\* \* \* \* \*